United States Patent [19]

Asano et al.

[11] Patent Number: 5,041,656

[45] Date of Patent: Aug. 20, 1991

[54] PREPARATION PROCESS OF (METH)ACRYLAMIDE

[75] Inventors: Shiro Asano, Takaishi; Mareo Tokunaga, Kaizuka; Yoshihiko Kambara, Takaishi, all of Japan

[73] Assignee: Mitsui Toatsu Chemicals, Inc., Tokyo, Japan

[21] Appl. No.: 565,900

[22] Filed: Aug. 10, 1990

Related U.S. Application Data

[63] Continuation of Ser. No. 219,886, Jul. 14, 1988, abandoned, which is a continuation of Ser. No. 839,374, Mar. 14, 1986, abandoned.

[30] Foreign Application Priority Data

Mar. 27, 1985 [JP] Japan ................................. 60-60830

[51] Int. Cl.$^5$ ........................................... C07C 231/06
[52] U.S. Cl. .................................................... 564/127
[58] Field of Search ..................................... 564/127

[56] References Cited

U.S. PATENT DOCUMENTS

| | | | |
|---|---|---|---|
| 3,766,088 | 10/1973 | Yoshimura | 252/412 |
| 3,928,440 | 12/1975 | Allain et al. | 260/561 |
| 3,985,806 | 10/1976 | Hashimoto et al. | 564/127 |
| 4,000,195 | 12/1976 | Svarz et al. | 502/301 |
| 4,056,565 | 11/1977 | Matsuda | 260/561 |

Primary Examiner—Carolyn S. Elmore
Attorney, Agent, or Firm—Fisher, Christen & Sabol

[57] ABSTRACT

A catalyst useful in the practice of a process, in which (meth)acrylamide is prepared through the hydration reaction between (meth)acrylonitrile and water in a suspended liquid-phase bed of a Raney copper catalyst, has been obtained by leaching a Raney copper alloy in the presence of the Raney copper catalyst which has been deteriorated. The above useful catalyst has higher performances, compared with a catalyst obtained by conventionally leaching the Raney copper alloy alone, has satisfactory handling properties in settling and filtering, and can significantly reduced the amount of catalyst to be discarded.

4 Claims, No Drawings

PREPARATION PROCESS OF (METH)ACRYLAMIDE

This application is a continuation of Ser. No. 07/219,886 filed July 14, 1988, now abandoned, which is a continuation of Ser. No. 06/839,374 filed Mar. 14, 1986, now abandoned.

BACKGROUND OF THE INVENTION a) Field of the Invention:

This invention relates to a process for synthesizing acrylamide or methacrylamide [hereinafter collectively called "(meth)acrylamide"] by hydrating acrylonitrile or methacrylonitrile [hereinafter collectively called "(meth)acrylonitrile"] in a suspended liquid-phase bed of a Raney copper catalyst, and more specifically, to a process for preparing a Raney copper catalyst suitable for use in the above reaction.

b) Description of the Prior Art:

It has been known that Raney copper can be used as a catalyst for the hydration reaction between (meth)acrylonitrile and water, for example, from U.S. Pat. No. 4,056,565 and Japanese Patent Publication No. 11657/1980. As also known from U.S. Pat. No. 3,766,088 for instance, this catalyst gradually loses its activity and in the hydration reaction of acrylonitrile for example, more and more byproducts such as $\beta$-hydroxypropionitrile (hereinafter abbreviated as "HPN") are produced while it is continuously used over a long period of time. According to the present inventors' finding, the settleability and filterability (hereinafter called "settling and filtering properties" for the sake of brevity) of this catalyst from the reaction mixture deteriorate progressively as its application time becomes longer. This feature is also extremely inconvenient for its application in the industry.

In the above U.S. Pat. No. 3,766,088, a process is proposed to regenerate a deteriorated metallic copper catalyst with a chemical solution such as a solution of caustic soda. This process is however impractical not only because the activity restoration of the catalyst is insufficient but also because the process is uneconomical due to its need for some regeneration facilities and chemical solution and the settling and filtering properties of the catalyst are, on the contrary, aggravated by the regeneration.

Due to lack of any suitable regeneration processes as mentioned above, the catalyst which has been used for a long period of time, in other words, which has been deteriorated through its use in the reaction has to be taken out of the reaction facilities and then discarded in a certain way, for example, by its disposal. No economical process has however yet been known to discard such a heavy metal in a harmless state.

SUMMARY OF THE INVENTION

An object of this invention is to regenerate a deteriorated catalyst, which has been used in the industrial production of (meth)acrylamide, so as to restore its activity and at the same time, to reduce byproducts.

Another object of this invention is to provide a process in which the settling and filtering properties of the catalyst are restored by its regeneration, the high costs for facilities and chemical reagent for its regeneration are lowered, and the volume of waste catalyst to be discarded can be reduced significantly or even to zero by its regeneration and reutilization.

The above-described objects of this invention can be attained by the following process:

In a process for preparing (meth)acrylamide through the hydration reaction between (meth)acrylonitrile and water in a suspended liquid-phase bed of a Raney copper catalyst, the improvement wherein a Raney copper alloy is leached in the presence of the Raney copper catalyst which has been deteriorated during the reaction, and the resultant mixed catalyst is then used to proceed further with the reaction.

DETAILED DESCRIPTION OF THE INVENTION

The mixed catalyst (hereinafter called "leached and regenerated catalyst" for the sake of clarity) obtained and used in the present invention can achieve better performance than a catalyst (hereinafter called "conventionally leached catalyst" for the sake of clarity) obtained by leaching the same Raney copper alloy in a usual manner. Namely, the following effects have been brought about by the present invention.

(1) The leached and regenerated catalyst has higher activities and produces less byproducts such as HPN, compared with the conventionally leached catalyst. Further, it is as excellent as the conventionally leached catalyst in terms of the selectivity to (meth)acrylamide.

(2) The settling and filtering properties of the leached and regenerated catalyst are also as good as the conventionally leached catalyst. It can hence be used in an industrial apparatus in the same manner as the conventionally leached catalyst.

(3) The catalyst preparation and regeneration can be simultaneously and economically conducted without need for any special facilities or reagents other than usual facilities and reagents employed for the preparation of Raney copper.

(4) The volume of waste catalyst to be discarded can be reduced even to zero. This is economically advantageous.

The advantages of the present invention can therefore be considered to be extremely large.

The present invention will hereinafter be described in more detail.

In the present invention, the reaction in which acrylonitrile is hydrated into acrylamide is represented by the following equation (1) whereas the reaction in which HPN, one of the principal byproducts, is formed is represented by the following equation (2).

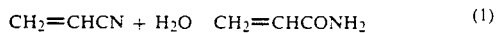

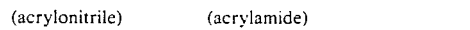

(acrylonitrile)   (acrylamide)

(HPN)

The hydration reaction between methacrylonitrile and water is also represented by similar equations.

The term "Raney copper catalyst" as used herein means a catalyst obtained by leaching a so-called Raney copper alloy with an aqueous solution of a basic compound such as sodium hydroxide to elute soluble components from the alloy and then washing and removing most of the thus-eluted components and excess basic compound from the resultant leached catalyst with water or the like. Its principal catalytic component is considered to be metallic copper. As soluble components in the Raney copper alloy, aluminum, zinc or the like is used with aluminum being preferred.

In order to enhance the activities and selectivity of the catalyst, it may additionally contain a second component such as nickel, molybdenum, silver, palladium or the like. In the case of nickel for example, a ternary Raney alloy of the aluminum-copper-nickel system is leached into a secondary Raney catalyst of the copper-nickel system for use in the intended reaction. Here, no problems or inconvenience will arise even if the content of the second component such as nickel is higher than that of copper (for example, nickel:copper=7:3).

Since the catalyst is used in a suspended liquid-phase bed, it must be either powdery or granular. Catalysts having particle sizes of 40 mesh or smaller are generally used. To obtain such a particle size, it is necessary to leach a powdery or granular Raney copper alloy or to leach a Raney copper alloy of a greater grain size, followed by its grinding into smaller grains or particles.

The leaching and regenerating operation of the present invention can be effected simply by adding the deteriorated catalyst to a leaching tank upon leaching the Raney copper alloy in a usual manner. A description will next be made on a usual leaching process. It can be used, substantially as is, in the leaching and regenerating process of the present invention.

As illustrative examples of the basic compound useful for the leaching operation, may be mentioned inorganic compounds such as sodium hydroxide, sodium carbonate, potassium hydroxide and potassium carbonate as well as organic amine compounds such as trimethyl amine. Among these basic compounds, sodium hydroxide is suitable.

Incidentally, compounds such as sodium chloride, ammonium chloride and calcium chloride are disclosed as regenerating reagents for metallic copper catalysts in the above-mentioned U.S. Pat. No. 3,766,088. One or more of these compounds may be used in combination with the above-described basic compound.

Since each of these basic compounds is consumed owing to its reactions with soluble components contained in the Raney copper alloy to be leached, it is used usually in an amount either equal to or more than its reaction equivalent. When an aluminum-copper alloy is leached and regenerated with an aqueous solution of sodium hydroxide, it is suitable to use 1-10 moles or preferably 1-3 moles of sodium hydroxide per atomic equivalent of aluminum. Any amounts smaller than the lower limit do not permit sufficient leaching and regeneration and result in such inconvenience that aluminum compounds are caused to precipitate. Any amounts greater than the upper limit lead to wasting of sodium hydroxide and are hence uneconomical.

These basic compounds are used, usually, as aqueous solutions of 1-50 wt.% in concentration. In the case of sodium hydroxide for example, 10-40 wt.% is preferred. No particular inconvenience will however arise even if sodium hydroxide is used in concentrations lower than the lower limit, except that use of such lower concentrations require an excessively-large leaching tank. No particular inconvenience will arise either even if sodium hydroxide is in concentrations higher than the upper limit, except that sodium hydroxide or a compound, which is to be formed by the leaching, may exist in excess of its own solubility and the flowability of the solid-liquid mixture, the leaching and regeneration of which are under way, may be hence reduced.

The reaction between aluminum and sodium hydroxide is a dangerous reaction, because the reaction is exothermic and gives off hydrogen gas. It is thus necessary to carry out the reaction while controlling the reaction velocity. As one method for controlling the reaction velocity, it is general to add the Raney copper alloy little by little to the leaching tank, in which caustic soda has been charged in advance, or in the opposite order, to gradually add caustic soda to the leaching tank with the alloy and water charged therein while cooling the contents of the leaching tank by a jacket or coil. As a procedure for adding the deteriorated catalyst to the above system, it may be charged beforehand in the leaching tank or may be added little by little along with the Raney copper metal or caustic soda. Since foaming tends to occur in the leaching tank due to generation of hydrogen gas and the stirring, it is recommended to use a defoaming agent as needed.

No particular limitation is imposed on the mixing ratio of the deteriorated catalyst to the Raney copper alloy. In the case of a 1:1 alloy of aluminum and copper for example, a weight ratio of about 10:1-1:10 is suitable. It is not economical to use the deteriorated catalyst in any amounts smaller than the above lower limit. Catalysts of sufficient properties may however not always be obtained if the deteriorated catalyst is used in any amounts greater than the upper limit.

Similar to usual leaching processes, it is suitable to conduct the leaching and regenerating operation at room temperature $-120°$ C. for 0.5-10 hours. It is preferable to maintain the contents of the leaching tank at a similar temperature for a similar period of time, namely, to conduct so-called aging.

Remaining sodium hydroxide and resultant aluminum compounds are then removed from the thus-leached and regenerated catalyst by a usual method such as decantation with water, thereby obtaining the leached and regenerated catalyst in a water-containing state. It is then used in the intended hydration reaction of (meth-)acrylonitrile.

By the way, it is desirable to avoid contact of the catalyst with oxygen or an oxygen-bearing gas during the above-described preparation process of the catalyst and its storage. Oxygen undergoes a reaction with the catalyst and below a certain limited degree of the reaction, the activities of the catalyst are not impaired or on the contrary, are enhanced. Beyond the above-mentioned degree, its activities are impaired and more by-products such as HPN are caused to form. In addition, the setting and filtering properties of the catalyst from the reaction mixture are deteriorated by its excessive contact with oxygen.

The process in which acrylamide is synthesized from acrylonitrile by using a Raney copper catalyst may be outlined as follow:

The catalyst is maintained in a state suspended in the reaction mixture and is used either in a flow or batch system. Principally, acrylonitrile and water may be fed at any desired weight ratio for their reaction. However, their weight ratio may be preferably in a range of 60:40-5:95 or more preferably in a range of 50:50-10:90. The preferable reaction temperature may range from 70° C. to 150° C. with a range of 90-140° C. being more preferred. The conversion of acrylonitrile to acrylamide may be preferably 20-98% or more preferably 30-95%.

At the above-described weight ratio of acrylonitrile to water, reaction temperature and conversion of acrylonitrile, unreacted acrylonitrile, unreacted water and resultant acrylamide may separate into two phases instead of forming any homogeneous liquid system. To avoid this, the above-synthesized acrylamide may be added back as a co-solvent to the reaction system or another inert co-solvent may be added.

The interior of the reactor is maintained under a total pressure which is the sum of the vapor pressures of the reactants and reaction product at the above-mentioned temperature and composition and the pressure of an inert gas such as nitrogen. The total pressure generally ranges from normal pressure to 20 atm. Since oxygen dissolved in the water-containing catalyst, acrylonitrile, water, co-solvent and the like, which are charged in the reactor, impairs the activities of the catalyst, deteriorates the setting and filtering properties of the catalyst from the reaction mixture and increases byproducts such as HPN as mentioned above, it is desirable to remove oxygen sufficiently before their feeding to the reactor. For the same reasons, it is desirable to maintain the interior of the reactor in an oxygen-free atmosphere.

The thus-obtained reaction mixture is then passed to a usual evaporation or distillation step, in which a concentrated aqueous solution of acrylamide is obtained and at the same time, substantially the whole amount of unreacted acrylonitrile and a portion of water are distilled and recovered. The thus-recovered acrylonitrile and water are usually reutilized as raw materials, although they may also be used for other purposes.

On the other hand, the catalyst which has been used in the suspended state is repeatedly used for the reaction by separating it from the reaction mixture prior to delivering the reaction mixture to the abovementioned distillation or evaporation step or by separating it subsequently from the concentrated solution obtained in the distillation or evaporation step. A major portion of the thus-separated catalyst is allowed to remain in the reaction system or is recycled to the reaction system for its reutilization, while the remaining portion of the separated catalyst is taken out of the reaction system and is passed to the leaching and regenerating step of this invention. Alternatively, the reaction may be halted and the whole catalyst may be subjected at a similar mixing ratio to the leaching and regenerating treatment of this invention.

As a separation method of the catalyst from the reaction mixture, it is general to rely upon settling and filtration. As a specific settling method, may be mentioned to use a thickener provided either inside or outside the reactor, to make use of a centrifugal settling machine, or so. As a specific filtration method on the other hand, may be mentioned to use a filter provided either inside or outside the reactor, to employ a centrifugal separator or the like. These methods may also be used in combination.

A detailed description has been made above primarily on the hydration reaction of acrylonitrile. The hydration reaction of methacrylonitrile is substantially the same as the hydration reaction of acrylonitrile and is hence carried out in a similar manner.

The Raney copper catalyst is progressively deteriorated in settling and filtering properties while using for long period of time, as the results it is no longer settled efficiently in the above-mentioned settling step so that it may be excessively carried away with the reaction liquid. The catalyst also becomes difficult to filter so that it may pass through the filter or block the filter in the above-mentioned filtration step. Needless to say, these problems prevent stable operation and induce serious economical damages. These problems can be efficiently improved by the present invention. Hence, the term "deteriorated catalyst" as used in the above explanation is not necessarily limited to that resulted from the use of the conventional leached catalyst for a certain period of time in the hydration reaction of (meth)acrylonitrile but also includes a catalyst resulted from further use of the leached and regenerated catalyst for a certain period of time in the same reaction. The performance of the leached and regenerated catalyst obtained from the further use of the first-mentioned leached and regenerated catalyst is not different from that of the first-mentioned leached and regenerated catalyst. By repeating the reutilization of deteriorated catalyst in the above manner, it is hence possible to reduce the amount of waste catalyst, which has to be discarded, substantially to zero and to lower leapingly the consumption of the conventionally leached catalyst of a high price. The process of this invention is therefore extremely advantageous.

The process of this invention will hereinafter be described in further detail by the following Examples.

EXAMPLE 1

I. Preparation or catalyst, etc.

(A) Conventionally leaching of catalyst

In a 5-l flask fitted with a stirrer, 2.22 kg of a 25 wt.% aqueous solution of caustic soda was charged. The aqueous solution was then heated to about 50° C. Meanwhile, a 50:50.(by weight ratio) alloy of aluminum and copper was crushed to powder and coarse particles were sifted off through an 80-mesh sieve to provide 400 g of the alloy in a powder form. While maintaining the internal temperature of the flask at 50–60° C. by stirring the aqueous solution and cooling it over an external bath, the alloy powder was added little by little into the flask over about 2 hours. Thereafter, the internal temperature was maintained at 50–60° C. for about 1 hour to subject the reaction product to aging. The reaction mixture was left over in standstill, the resultant supernatant was discarded, and 2 l of purified water was added to the residue, followed by its stirring for 30 minutes. This decantation was repeated an additional 3 times. Upon completion of the decantation, the supernatant was discarded to obtain about 200 g of a conventionally leached catalyst in a state dipped in water. During the above operation and the subsequent storage, the flask and other vessels were kept under a nitrogen atmosphere to avoid contact of the catalyst with air.

(B) Preparation of deteriorated catalyst

By using a catalyst prepared in the same manner as in the preparation (A) of the conventionally leached catalyst except that the scale of the preparation was increased by 10 times, a continuous reaction run was conducted for 45 days in the same manner as the flow-type reaction test in Example 2, which will be described herein, except that the scale of the reaction was increased by 10 times.

Thereafter, the reaction was halted and a portion of the catalyst was taken out. The catalyst was washed 4 times with purified water by decantation, thereby obtaining about 1,000 g of the catalyst in a deteriorated form. During the withdrawal, washing and subsequent storage of the catalyst, the catalyst was kept under a nitrogen atmosphere so as to avoid its contact with air.

(C) Conventionally regenerated catalyst

The above-prepared deteriorated catalyst was regenerated in the same manner as that described in U.S. Pat. No. 3,766,088. Namely, about 200 g of the deteriorated catalyst was charged along with 2.22 kg of a 25 wt.% aqueous solution of caustic soda in a 5-l flask. The contents were maintained at 50-60° C. for 3 hours by stirring and heating with unexternal bath and then decanted repeatedly 4 times with purified water, thereby obtaining about 200 g of the catalyst in a regenerated form. During the regeneration, washing and subsequent storage of the catalyst, the catalyst was maintained under a nitrogen atmosphere so as to avoid its contact with air.

(D) Leaching and regeneration of catalyst

In a 5-l flask fitted with a stirrer, about 200 g of the above-prepared deteriorated catalyst and 2.22 kg of a 25 wt.% aqueous solution of caustic soda were charged, followed by their heating to about 50° C. There was also provided 400 g of Raney copper alloy powder, which was of the same type as that employed above in the preparation of the conventionally leached catalyst. Then, while maintaining the internal temperature of the flask at 50-60° C. by stirring the contents and cooling same over an external bath, the alloy powder was added little by little into the flask over 2 hours, followed by maintenance of the internal temperature at 50-60° C. for about 1 hour to effect aging. Thereafter, decantation was repeated 4 times in the same manner as in the preparation of the conventionally leached catalyst to obtain about 400 g of the catalyst in a leached and regenerated form. During the above operation and subsequent storage, the catalyst was maintained under a nitrogen atmosphere to avoid its contact with air.

II. Batch-type reaction tests

The following batch-type reaction tests were respectively conducted by using the above-prepared 4 types of catalysts. In a 100-ml flask fitted with a stirrer, thermometer and reflux condenser, 6.6 g of acrylonitrile, 36 g of water and 7 g of the catalyst was charged. Since the catalyst was prepared and stored in a state dipped in water, about 7 g of water was accompanied upon charging the catalyst. Thus, this water was beforehand deducted from the weight of water to be charged separately, so that the total weight of water was controlled at 36 g.

The flask was heated to about 70° C. over an external bath. Thereafter, by controlling the temperature of the external bath, the flask was maintained at 70°-72° C. to conduct the reaction for 2 hours. The flask was then cooled to terminate the reaction. The reaction mixture was then analyzed by gas chromatography to determine the conversion of acrylonitrile to acrylamide and the proportion of HPN to acrylamide (the by production rate of HPN). Results are shown in Table 1.

Oxygen dissolved in the raw materials, acrylonitrile and water, was removed beforehand and the reaction system was kept under a nitrogen atmosphere so as to avoid contact of the catalyst to oxygen in the above-described operation.

TABLE 1

| | Run No. | | | |
|---|---|---|---|---|
| | 1-1 (Comp. Ex.) | 1-2 (Comp. Ex.) | 1-3 (Comp. Ex.) | 1-4 (Example) |
| | Catalyst | | | |
| | Conventional leached cat. | Deteriorated catalyst | Conventional regenerated cat. | Leached and regenerated cat. |
| Conversion (%) | 65 | 36 | 57 | 69 |
| Byproduction rate of HPN (%) | 0.07 | 0.16 | 0.15 | 0.07 |

EXAMPLE 2

The following flow-type reaction tests were conducted by using the 4 types of catalysts of Example 1 respectively.

Charged in a reactor made of stainless steel and equipped with a stirrer and a built-in catalyst filter was 150 g of the catalyst. Acrylonitrile and water from which dissolved oxygen had in advance been removed by blowing nitrogen gas thereinto were then fed respectively at velocities of 300 g and 700 g per hour. They were reacted while stirring and suspending the catalyst and maintaining the catalyst system at 120° C. As a reaction accelerator, copper nitrate was added to the raw material water in such an amount that the concentration of copper nitrate reached 30 ppm in terms of the anhydrous salt on the reaction mixture. The reaction mixture was allowed to pass through the catalyst filter, and to flow out as a liquid substantially free of the catalyst. The reaction mixture was then led to a reaction mixture reservoir. The reaction mixture was drawn out of the reservoir once a day.

The reaction mixture which flowed out of the reactor was sampled every second day. The sampled reaction mixture was analyzed by gas chromatography to determine the conversion and the by production rate of HPN.

The pressure of the reaction mixture reservoir was always maintained at about 4 Kg/cm$^2$ by either charging or discharging nitrogen gas. In this manner, the pressure of the reactor became somewhat higher than 4 Kg/cm$^2$. This pressure difference ($\Delta P$) corresponds to the resistance of the filtration surface of the catalyst filter. Although $\Delta P$ was close to 0 on the incipient day of the reaction, it increased as the reaction was continued. The test was stopped when $\Delta P$ exceeded 2 Kg/cm$^2$.

Results of the above reaction tests are shown in Table 2. The leached and regenerated catalyst of the present invention was superior to all the other catalysts.

TABLE 2

| | Run No. | | | |
|---|---|---|---|---|
| 2-1 (Comp. Ex.) | 2-2 (Comp. Ex.) | 2-3 (Comp. Ex.) | 2-4 (Example) |
| | Catalyst | | | |

TABLE 2-continued

| Number of days passed in reaction test | Conventional leached catalyst | | Deteriorated catalyst | | Conventional regenerated catalyst | | Leached and regenerated catalyst | |
|---|---|---|---|---|---|---|---|---|
| | Conversion (%) | Byproduction rate of HPN (%) | Conversion (%) | Byproduction rate of HPN (%) | Conversion (%) | Byproduction rate of HPN (%) | Conversion (%) | Byproduction rate of HPN (%) |
| Incipient day | 72 | 0.04 | 42 | 0.08 | 66 | 0.09 | 77 | 0.04 |
| 2 days | 67 | 0.05 | 39 | 0.09 | 62 | 0.09 | 74 | 0.04 |
| 4 days | 64 | 0.05 | 38 | 0.08 | 59 | 0.10 | 70 | 0.05 |
| 6 days | 60 | 0.04 | 36 | 0.09 | Test was stopped after 5 days due to increased ΔP. | | 68 | 0.04 |
| 8 days | 57 | 0.05 | 36 | 0.10 | | | 65 | 0.05 |
| 10 days | 54 | 0.06 | 34 | 0.10 | | | 63 | 0.05 |
| 12 days | 52 | 0.05 | 33 | 0.12 | | | 61 | 0.05 |
| 14 days | 50 | 0.06 | 31 | 0.11 | | | 59 | 0.06 |

EXAMPLE 3

Four types of catalysts were prepared in the same manner as in Example 1 except that acrylonitrile was changed to methacrylonitrile. Batch-type reaction tests similar to those conducted in Example 1 were carried out to determine the conversions of methacrylonitrile to methacrylamide. Results are summarized in Table 3. The leached and regenerated catalyst of this invention was superior to all the other catalysts.

TABLE 3

| | Run No. | | | |
|---|---|---|---|---|
| | 3-1 (Comp. Ex.) | 3-2 (Comp. Ex.) | 3-3 (Comp. Ex.) | 3-4 (Example) |
| | Catalyst | | | |
| | Conventional leached cat. | Deteriorated catalyst | Conventional regenerated cat. | Leached and regenerated cat. |
| Conversion (%) | 53 | 32 | 46 | 56 |

We claim:

1. In a process for preparing acrylamide or methacrylamide through the hydration reaction between acrylonitrile or methacrylonitrile and water in a suspended liquid-phase bed of a Raney copper catalyst used batchwise, the improvement wherein a Raney copper alloy comprised of 1:1 aluminum and copper by weight is leached in the presence of the Raney copper catalyst which has been deteriorated during the reaction, the ratio of the deteriorated catalyst to the Raney copper alloy being in the range of 10:1 to 1:10, and wherein the resultant mixed catalyst is then used to cause the reaction to proceed further.

2. The process as claimed in claim 1 wherein a major portion of the catalyst separated out from a reaction mixture is allowed to remain in or to be recycled to the reaction system, and the Raney copper alloy is leached in the presence of the remaining portion of the thus-separated catalyst.

3. The process as claimed in claim 1 wherein upon leaching, sodium hydroxide is used in an amount of 1 to 10 moles per atomic equivalent of aluminum in the Raney copper alloy.

4. The process as claimed in claim 1 wherein in the hydration reaction, the weight ratio of acrylonitrile or methacrylonitrile to water ranges from 60:40 to 5:95, the reaction temperature ranges from 70° to 150° C., and the conversion of acrylonitrile ranges from 20 to 98 percent.

* * * * *